United States Patent [19]

Gabbay

[11] 4,381,771

[45] May 3, 1983

[54] FEMALE CONTRACEPTIVE

[75] Inventor: Shlomo Gabbay, Hartsdale, N.Y.

[73] Assignee: Kedma, Incorporated, Hartsdale, N.Y.

[21] Appl. No.: 333,049

[22] Filed: Dec. 21, 1981

Related U.S. Application Data

[63] Continuation-in-part of Ser. No. 174,224, Jul. 31, 1980, abandoned, which is a continuation-in-part of Ser. No. 950,162, Oct. 10, 1978, abandoned, which is a continuation of Ser. No. 764,765, Feb. 2, 1977, abandoned.

[51] Int. Cl.³ .............................................. A61F 5/46
[52] U.S. Cl. ................................. 128/129; 128/127; 604/330
[58] Field of Search .............................. 128/127–131, 128/285, 295

[56] References Cited

U.S. PATENT DOCUMENTS

| 158,891 | 1/1875 | Bennett et al. | 128/127 |
|---|---|---|---|
| 535,568 | 3/1895 | Ware | 128/129 |
| 578,210 | 3/1897 | Charlton | 128/129 |
| 1,162,568 | 11/1915 | Carey | 128/129 |
| 2,061,384 | 11/1936 | Manegold | 128/285 |
| 2,699,781 | 1/1955 | Koch | 128/295 |
| 2,811,153 | 10/1957 | Maki | 128/127 |
| 2,823,669 | 2/1958 | Kunnas | 128/127 |
| 2,836,177 | 5/1958 | Sells | 128/127 |
| 3,157,180 | 11/1964 | Bakunin | 128/285 |
| 3,512,528 | 5/1970 | Whitehead et al. | 128/285 |

FOREIGN PATENT DOCUMENTS 19593 of 1894 United Kingdom ................ 128/127

OTHER PUBLICATIONS

Population Reports, Series H, No. 4, Jan. 1976, Publ. Population Information Program, GWU Med. Ctr.

Primary Examiner—C. Fred Rosenbaum
Attorney, Agent, or Firm—Jordan B. Bierman; Linda Bierman

[57] ABSTRACT

A female contraceptive, cervical cover, including a dome-like main portion which is shaped to cover the cervix, long extending lips which form a one-way valve to permit waste material to flow out of the cervix and an outwardly biased collar which holds the cover securely to the walls of the vagina surrounding the cervix, without exerting any substantial pressure on the cervix.

34 Claims, 21 Drawing Figures

FEMALE CONTRACEPTIVE

This application is a continuation-in-part of my application Ser. No. 174,224 filed July 31, 1980 and now abandoned which was a continuation-in-part of my application Ser. No. 950,162 filed Oct. 10, 1978 and now abandoned which was in turn a continuation of my original application Ser. No. 764,765 filed Feb. 2, 1977 and now abandoned.

BACKGROUND OF THE INVENTION

There have been many attempts at producing a female contraceptive that can remain in place for long periods of time without the need for removal.

The five basic types of female contraceptives now on the market are the diaphragm, the contraceptive pill, containing estrogen or progesterone, contraceptive foaming agents, cervical caps and intra-uterine devices or I.U.D.'s. Diaphragms are reliable but must be continually removed each day; contraceptive pills reportedly have various undesirable side effects, including reports of carcinogenic damage to gall bladder and liver; foams fail to foam in many women and in any case are only reliable for one day at the most; I.U.D.'s are reliable but their reported side effects including excessive bleeding, possible sterility and other effects have lessened their desirability. Cervical caps are effective but must be removed every month for menstruation to take place. Moreover, many females have deformed cervices and cervical caps simply will not fit over such cervices.

The desire then has been to develop a contraceptive which could be left in place for a long period of time, two months to two years or more without any undesirable effects.

There have been attempts over the years to produce such a cervical cap. The desire was to produce a cervical cap that had a one-way valve so that discharge from the uterus through the cervix could pass outwardly into the vagina without sperm being able to penetrate the valve and enter the uterus. Two attempts are shown in U.S. Pat. Nos. 2,836,177, Sells and 3,952,737, Lippert, et al. Both of these cervical caps securely hold the cap to the cervix; the thought was apparently that if it were not securely held it would slip off. The Sells patent mentions that the cap is shaped so as to snugly fit upon and embrace the cervix, whereas the Lippert et al patent describes a device which is clamped or securely affixed to the cervix. The device includes grooves or flanges and an "O" ring to effect the fastening. The patent even describes the use of a bladder between the cap and the cervix to more securely hold the cap to the cervix. A secure hold apparently appeared to be a most desirable technique to prevent the cap from slipping off the cervix. Just the opposite is actually the case; holding the cap securely to the cervix will cause deterioration of the cervix including possibly gangrene and such infections as cervicitis and similar disorders. The cervix can withstand a reasonable amount of contact for a very short period of time, possibly up to a month; however, much beyond that period if anything is held tightly to the cervix, it will result in deterioration of the cervix.

Another reason why the prior art cervical caps with valves were held so tightly to the cervix was probably an attempt to duplicate the fit of the non-valve cervical caps; these caps had to be removed each month so that menses could take place. The caps held onto the cervix by suction, which was very often so great that air had to be introduced between the cap and the cervix to break the seal in order to remove the cap. However, even with these caps if they remained in place for more than one month cervical deterioration would take place.

Another problem with the prior art cervical caps with valves was that the cervix on many human females does not project very far. On these women, it is impossible to hold any cervical cap in place because the cervix does not extend far enough for the cap to be attached. Even the non-valve cervical caps could not be secured to these women. Also many women have deformed cervices, such as where one of the lips, the posterior lip, for example, is substantially longer than the anterior lip. This deformation as well as other irregularities in shape make it impossible to secure any cap to these women.

Another problem with cervical caps having valves, is that it is most important that the valves be constructed so that the distance between the entrance to the valve and the cervix be as great as possible so that if any semen enters the valve the distance it has to travel is so great and travel so difficult that it will not succeed in reaching the cervix. It is also important that the valve be constructed so that clots of blood or large clumps of material cannot wedge themselves in the entrance of the valve to hold the valve open so that semen can enter.

Thus the desire is to produce a cervical cover with a valve which fastens by holding securely to the vaginal wall surrounding the cervix without applying any significant pressure to the cervix, and which also has a path from its entrance to the entrance to the cervix which is so long and tortuous that if any semen accidentally entered the valve it could not reach the entrance to the cervix in the live condition.

SUMMARY OF THE INVENTION

It is, therefore, an object of this invention to provide a female contraceptive in the form of a cervical cover having one or more valves, which has no deleterious effect on the cervix.

It is a further object of this invention to provide such a cover which exerts almost no pressure on the cervix.

A still further object of the invention is to provide such a cover which is secured to the wall of the vagina surrounding the cervix.

Another object of this invention is to provide such a cover which is constructed so that if semen accidentally enters the valve the semen cannot reach the opening of the cervix in the live condition.

Another object of this invention is to provide such a cover which has long lips or cusps.

Still another object of this invention is to provide such a valve which will remain in place during distention of the vagina during coitus.

Yet another object of the invention is to provide such a cover where the lips or cusps are constructed so a clot of blood will not inadvertently hold them open so that semen can enter.

Yet another object of the invention is to provide such a cover which fills the area between the cervix and the vagina to prevent semen from collecting therein.

Yet another object of the invention is to provide such a cover which is readily insertable.

This invention envisions a female contraceptive in the form of a cervical cover which comprises a hollow body having a dome-like main section which somewhat conforms to the shape of the human cervix including an outwardly biased collar to hold the cover to the walls of the vagina and one or two pairs of extending lips or cusps which are connected together to define a passageway, said lips being normally biased together to contact each other so that the passage forms a normally closed valve. The lips are significantly long and made of material that semen has difficulty adhering to so that any semen which accidentally enters the valve cannot reach the cervix in the live condition. To cause the collar to exert pressure outwardly it may be inflatable with gas or be formed of expandable rubber, so that when in place the collar exerts pressure against the walls of the vagina surrounding the cervix without exerting any substantial pressure on the cervix. In one form of the invention, the inner wall of the collar may be thicker than the outer wall so that when inflated, force will be exerted outwardly and not inwardly. Also the collar can also be solid and include biasing means such as a spring. Means may also be provided to extend the path of any sperm which may inadvertently pentrate the valve. The cover is made of material which is compatible with the human body and especially material that semen does not readily adhere to, such as "Silastic" (clean medical grade) and different types of latex.

Other objects, features and advantages of the invention in its details of construction will be seen from the above and the following description and claims.

PREFERRED EMBODIMENT OF THE INVENTION

This invention relates to cervical covers and particularly cervical covers which have a valve and can be placed in the vagina for long periods of time. The present invention comprises a cover which is of a dome-shaped configuration, the dome being hemispherical, elongated, ovoid or of any other generally suitable configuration.

The dimensions of the valve will depend on the particular size, shape and irregularities of the cervix and the vagina.

Figure 1:
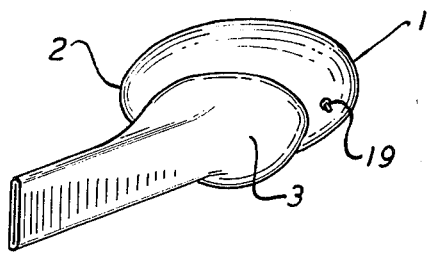
FIG. 1 is an overall perspective view of the cervical cover of this invention seen from the bottom.
Figure 2:
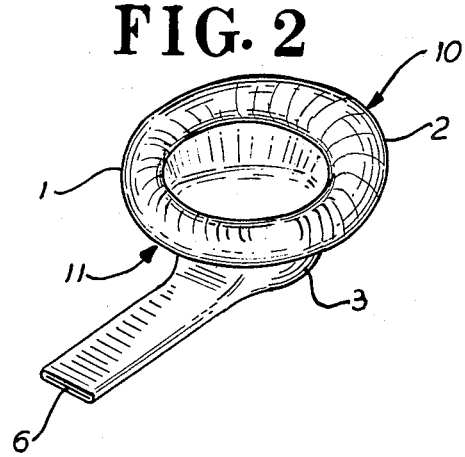
FIG. 2 is an overall perspective view of the cervical cover of this invention seen from the top.
Figure 3:
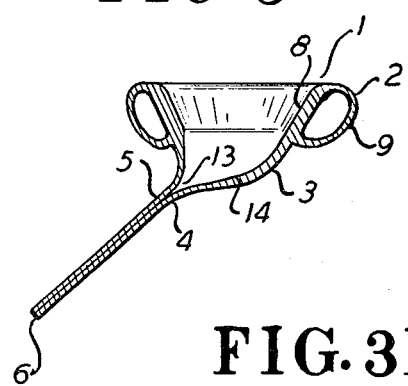
FIG. 3 is a cross-sectional view of the cervical cover of this invention.

The basic structure of the cover 1, FIGS. 1-3 comprises a surrounding collar 2, a hollow body having a dome-shaped section 3 and a pair of interconnected extending lips or cusps 4 and 5 which terminate in an opening 6. The entire cervical cover is molded or otherwise formed, usually as an integral member, of a flexible plastic that is compatible with the body in which it is being used. The plastic material is one that will not react in any way within the body or any of its fluids therein such as the menstrual fluids, blood and the mucous that are emitted by the cervix and the vagina. Typical plastics that meet these criteria are medical-grade silicone rubber manufactured by the Dow Corning Company of Michigan sold under the trademark "Silastic" and medical-grade latex.

Figure 4:
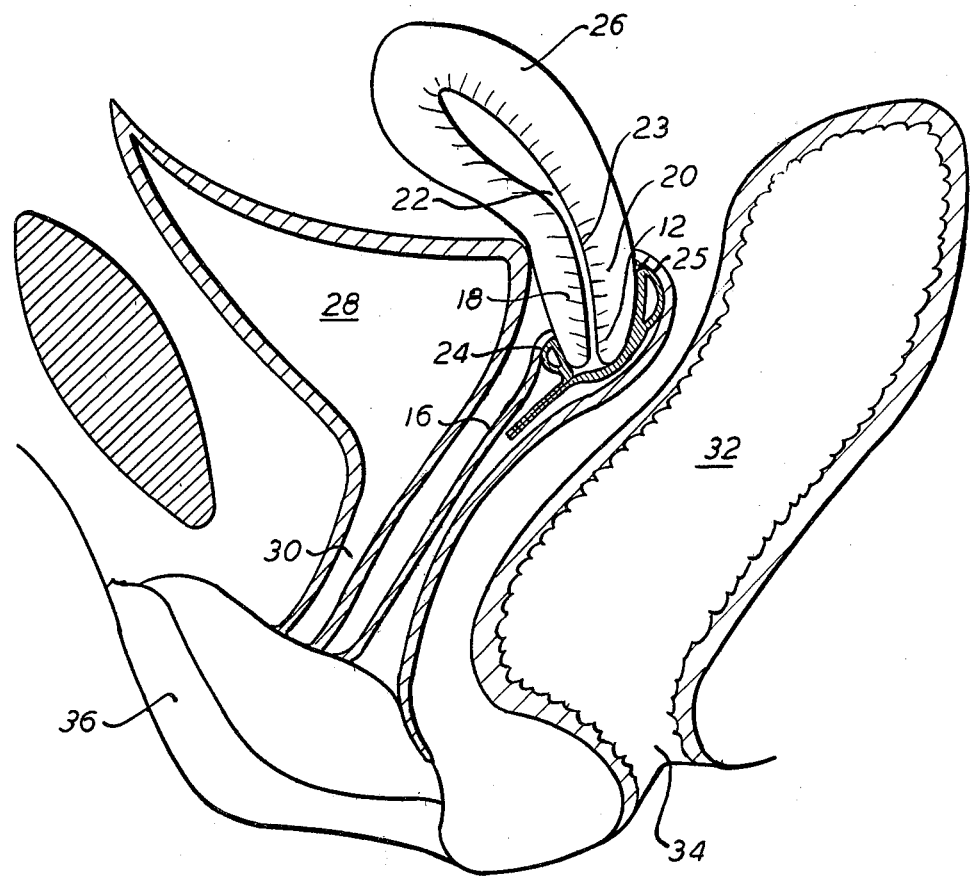
FIG. 4 is a side view of the human female pelvis with the cervical cover of this invention.
Figure 5:
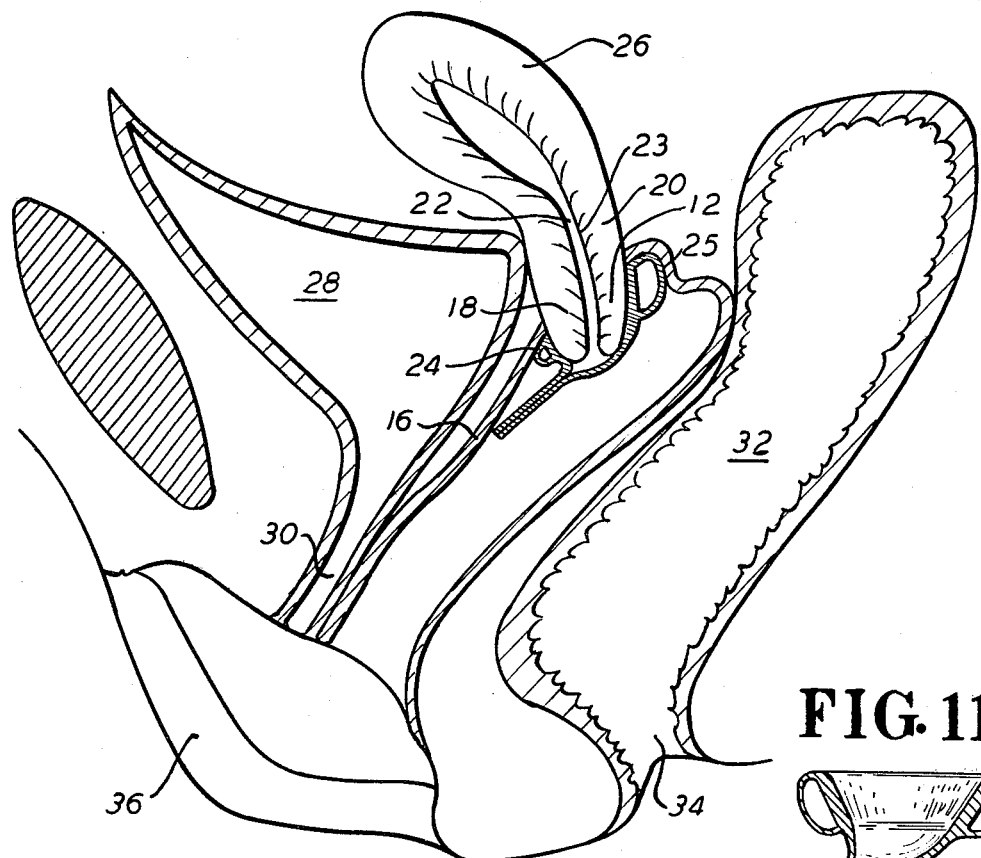
FIG. 5 is another view of FIG. 4 with the vagina distended as during coitus.

The dome or cup portion 13 is shaped basically to conform to the shape of the cervix of the human female. Human cervices vary in shape and size; they consist of two lips 12 (FIG. 4) which together form a dome-like projection which extends into the vagina 16. The projection however varies greatly between different individuals; sometimes it is positioned and shaped exactly as shown in FIG. 4; in other cases the projecting part is much smaller or at a different angle or more pointed or flatter or sometimes the lips will vary greatly in size, one being much longer than the other. Thus the dome-shaped portion of the cover may vary greatly in shape and size; however, it will be appreciated that while the dome-shaped portion should conform substantially to the shape of the cervix, it does not have to fit exactly; this is because the cervical cover of this invention is not held in place by being attached to the cervix, but is held in place by being secured to the walls of the vagina which surround the cervix. Thus there is no need for an exact fit. For ease in explaining the cervical cover of this invention and its location in the body, FIGS. 4 and 5 illustrate a cross-sectional view of the pelvis of the human female. Cervix 12 consists of posterior lip 20, and anterior lip 18 which extend into vagina 16. The lips define a passage 22 (os) into the uterus 26. In front of the uterus is the bladder 28 by which urine is excreted through the urinary canal 30. The rectum 32 is positioned in back of the vagina and terminates in the anus 34. Both the vagina and urinary canal open into an area between the labia 36. Positioned in front of the bladder is the pubic bone 31 which is part of the pelvis. The cervical cover of this invention is shown in place in FIGS. 4 and 5.

FIG. 4 illustrates the pelvis in the normal position and FIG. 5 illustrates the pelvis with the vagina distended as during coitus.

Figure 6:
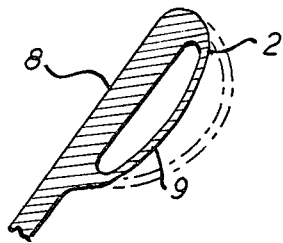
FIG. 6 is a detailed cross-sectional view of the collar before and after inflation.
Figure 7:
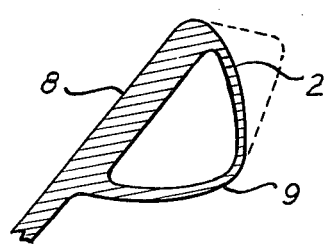
FIG. 7 is a detailed cross-sectional view of the collar before and after inflation.

The collar 2, which accomplishes the holding function is basically toroidal in shape, though it will vary greatly depending on the shape of the cervix and is of non-porous material. It is constructed so that it is soft and will exert pressure outwardly, that is away from the cervix, without exerting any significant pressure inwardly, toward the cervix. In other words, there probably will be no pressure exerted on the device but if there is any it will be insigificant compared with the pressure exerted by the cover on the walls of the vagina to hold the cover in place. In the embodiment shown in FIGS. 1–3 the collar is hollow having an inner wall 8, which is the wall of the dome, which is substantially thicker and more inflexible than the outer wall 9. Thus when pressure is introduced into the collar the outer wall 9 will expand and the inner wall will remain substantially unchanged. This will cause pressure to be exerted outwardly, to hold the cover in place by exerting pressure on the walls of the vagina. This is shown in more detail in FIG. 6 wherein the collar is shown in solid lines in the uninflated condition (walls 8 and 9 are very close to each other) and in dashed lines in the inflated condition. It will be seen that wall 8 being substantially flatter and thicker than wall 9, it substantially remains straight and unchanged in the inflated condition. This difference in thickness may be as much as 2, 3 or more times so that only wall 9 is biased outwardly with little, if any, effect on wall 8. FIG. 7 illustrates another embodiment where the collar inflates upwardly in a pointed configuration. Wall 8 is still substantially flat and straight and part of wall 9 now has inflated upwardly and outwardly. The distance and manner in which it will inflate will depend on its construction and upon the shape of the vagina in which it is intended to fit.

The posterior section 10 of the collar will generally be of a larger diameter than the anterior section 11. The reason for this, as will be explained in more detail with respect of FIG. 4, is that the posterior fornix 22 (cul-de-sac) of the vagina, is larger than the anterior fornix 24 and for a proper fit the posterior section of the collar should be larger than the anterior section. It will be appreciated that it is possible that because of the configuration of the cervix and the vagina the posterior section of the collar will be the same diameter as the anterior section and it is even possible that in some cases with certain types of deformed cervices the anterior section might be larger than the posterior section.

Figure 3A:
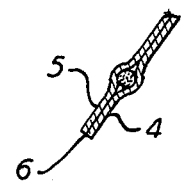
FIG. 3a is a cross-sectional view of part of the lips of the device of this invention.
Figure 3B:
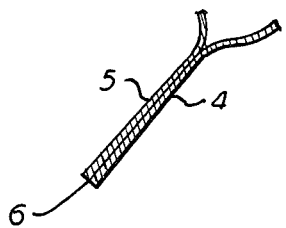
FIG. 3b is a cross-sectional view of another embodiment of the invention.
Figure 3C:
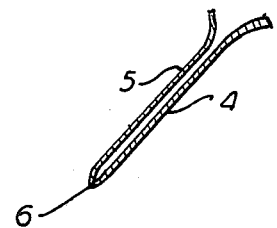
FIG. 3c is a cross-sectional view of another embodiment of the invention.

The extending lips or cusps 4 and 5 are long and planar; their length 6 will generally be about twice as long as their width. The plane of the lips will intersect the collar at a point very close to the point at which the posterior section of the collar is of maximum width. The width preferably is about as wide as the width of dome 3. It is desirable to make this as wide as possible so that the discharges from the cervix, such as menstrual fluid, will have the greatest possible area to flow out of the valve. These discharges must be able to flow out easily; if they cannot they will be kept in contact with the cervix and will lead to infections of the cervix. The lips are interconnected at their edges to define a flat linear opening ending in an outlet distal from the collar. They are also flexible and are slightly separated at the point 13, the point at which they join dome section 3 of the cover. As menstrual fluid fills this space 13 it will put pressure on the base 14 of the dome to cause lip 4 to be biased away from lip 5 to let the menstrual fluid pass out of the valve. The flexibility of the lips is such that if only a small amount of fluid is to be discharged, the section of the lips upstream of the fluid will close while that downstream will open. This is important in the passage of clumps of material such as blood clots. As shown in FIG. 3a., which illustrates a section of the lips, the lips will be closed above and below the clot and will open below the clot to permit the clot to be discharged. If the lips were very short or somewhat inflexible, a blood clot could keep the lips separated throughout their length and semen could pass through the opening and into the cervix. To further prevent semen from travelling to the cervix, the lips are made long, probably about 2–5 centimeters and are made of a plastic material as aforementioned which is non-adhesive to semen so that if any semen does accidentally enter the passage between lips 4 and 5, it will have great difficulty reaching the cervix. It will not only have to travel the great distance between the lips but will also have to separate the lips in its travel upward toward the cervix and, finally, will have to travel on a material to which it cannot attach easily. The lips may also be constructed as shown in FIG. 3b, so that they are thinner towards the dome than at the bottom opening. The lips then will readily open to permit fluids to pass outwardly but will remain closed at exit 6 to prevent semen from entering. Also as shown in FIG. 3c, the lips can be normally slightly separated throughout their length except at the outer end 6 where they form flaps, which are inclined together and may be made of slightly thicker material. The discharged material will then readily flow through the valve and the pressure of the material will open the flaps to discharge the material.

The lips are positioned at an angle of about 45° with respect to the axis of the collar. This will position the lips as shown in FIG. 4 so that they may slightly contact the walls of the vagina when the vagina is in the normally closed position of FIG. 4. It will be appreciated that the angle will vary depending on the particular shape and position of the cervix and its position in the vagina. It will also be seen that as shown in FIG. 5, when the vagina is extended as during coitus or upon the insertion of a catemenial device during menses, the lips will not interfere with the member being inserted.

Figure 10:
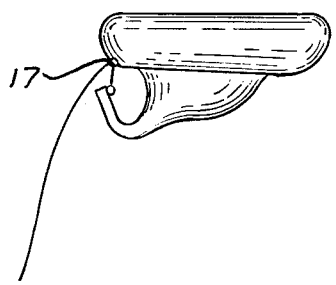
FIG. 10 is a cross-sectional view of another embodiment of the invention.

To further close the lips a string may be provided as shown in FIG. 10. The string may be made of thin plastic, such as nylon, which is compatible with the human body. The string is attached to the anterior lip 5 proximate its end 7 and placed through an eyelet 17 which is positioned on the outer lower surface of the anterior position of collar 2. The string will be of a length sufficient to reach the end of the vagina without extending outside of the vagina. When the string is pulled, the lips will move from the normal position which is the same as that shown in FIG. 3 to the folded position as shown in FIG. 10. This will place a fold in the lips and further prevent semen from entering therein.

Figure 12:
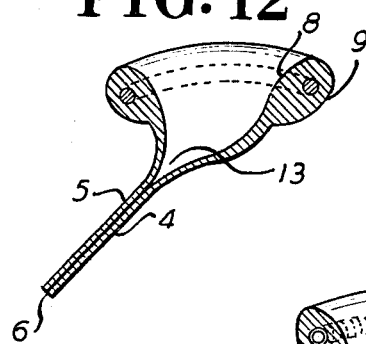
FIG. 12 is a cross-sectional view of an embodiment using a spring in the collar.
Figure 13:
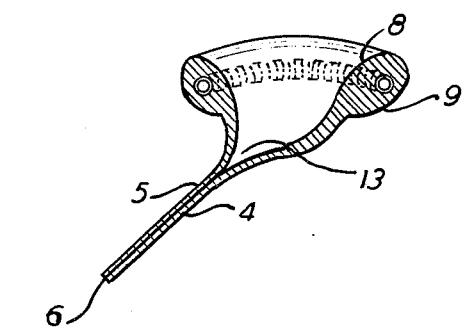
FIG. 13 is a cross-sectional view of another embodiment using a spring in the collar.

The collar as aforementioned is made so that it biases outwardly. This can be accomplished by many suitable methods including inflating the collar, or by using a spring which is inserted or molded into the collar and which biases outwardly. The spring can be a coiled metal or plastic spring as shown in FIG. 13 or can be a round metal or plastic spring as shown in FIG. 12. These latter springs will also bias the collar outwardly so that the cervical cover is supported on the walls of the vagina and not on the cervix. These springs can also be combined with an inflatable collar to increase the outward biasing force. Also if desired the plastic material of the collar itself can be molded so that it is slightly larger than the surrounding walls of the vagina so that it normally biases outwardly. This molding can also be combined with the inflation and/or spring to achieve the desired degree of biasing. Also part of the collar can be inflated and part spring biased or any other suitable combination.

With the inflation method the collar can be inflated when it is molded or can be inflated subsequently either before placement in the vagina or after placement. The collar can be inflated with air or other suitable gas or liquid fluid such as a foaming agent (e.g. Dow Corning Silicon foam or Polyurethane foam) or a combination thereof. If a gas is used, any suitable method of inflation can be employed; for example a projection of material can be molded into the collar as shown at 19 in FIGS. 1-3; the projection can be solid with a hole therethrough. A syringe or needle is then inserted through the projection and air or other gas or fluid is inserted into the collar to inflate it. If or when it is desired to remove the cover, if the inflation method is used, the collar may be ruptured and the cervical cover removed.

Figure 4A:
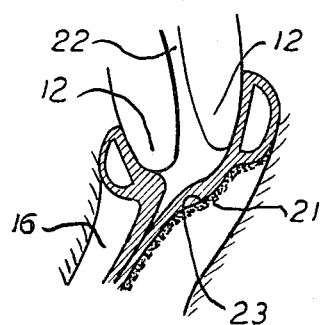
FIG. 4a is a cross-sectional view of the cervical cover of the invention with semen thereon.

It will be appreciated that when the cervical cover is in position as shown in FIGS. 4-5, the collar will substantially fill the fornix; the posterior section of the collar will fill the posterior fornix and the anterior section will fill the anterior fornix. These parts of the vagina are wider and thereby once the collar is in place it will tend to stay there without moving. Normally when semen enters the vagina it collects in the posterior fornix and slowly flows over the cervix to enter the cervix. Even with cervical caps the semen will still collect in the posterior fornix and flow over the cervical cap. This opens the possibility with prior cervical caps that since all of this collected semen will pass over the cervical cap, for some semen to creep in between the cap and the cervix wall and pass under the cap so that it can enter the opening of the cervix. With the present cover the posterior fornix is filled with the collar; the semen will therefore not be able to collect in the posterior fornix and will simple slide down the outer surface of the cervical cover and out of the vagina. This is shown in more detail in FIG. 4a; semen 21 will travel down the outer surface 23 of the cover and will not be able to collect in the fornix or any other location. The material of the cervical cover, as aforementioned, is nonadhesive to semen and thus the semen will slide over its surface and out of the vagina very quickly. By not being able to collect in the fornix there is no likelihood, as there was with prior art cervical caps, of the semen slipping between the cap and the cervix and entering the opening of the cervix.

This also overcomes the need for a spermicidal cream or jelly since the purpose of such cream or jelly is to kill the sperm that collect in the fornix. Further because the semen cannot collect together they will not be able to remain in the vagina for any period of time. This will tend to keep the vagina cleaner and reduce the chance of infection.

When the device is in place, the posterior section of the collar will fit into the posterior fornix 22 and the anterior section will fit into the anterior fornix 24 with the collar biasing outwardly, to put pressure on the walls of the vagina to hold the collar in place. The cervical cover will thus surround the cervix without applying any significant pressure to it.

Figure 8:
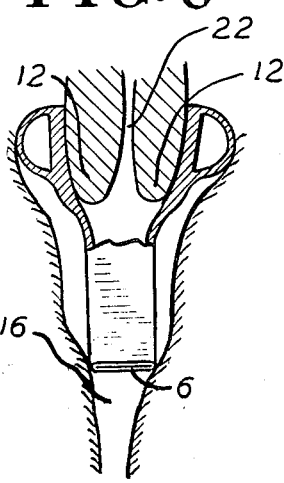
FIG. 8 is frontal view of a cervix with the cervical cover of this invention in place.
Figure 9:
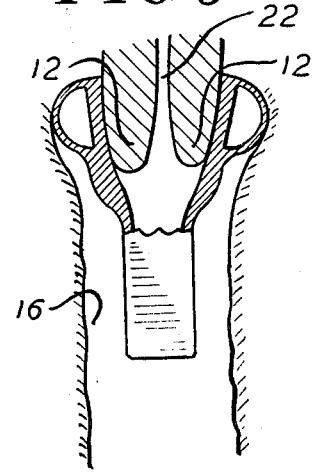
FIG. 9 is a frontal view of a cervix with the cervical cover of this invention in place and the vagina distended.

FIGS. 8 and 9 illustrate a front view of the cervix and vagina respectively in the normal position as shown in FIG. 4 and the distended position of FIG. 5. In these views it will be seen that the collar 3 holds securely to the walls of the vagina without any pressure on the cervix and that the lips of the cover do not interfere with the walls of the vagina.

Figure 11:
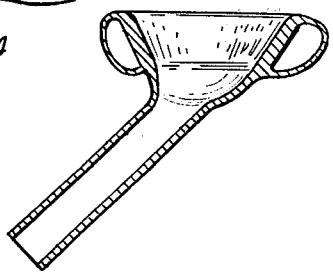
FIG. 11 is a cross-sectional view of another embodiment of the invention.

Also alternatively the extended lips 38 can be positioned as shown in FIG. 11 so that they are rotated substantially 90° from the construction of FIGS. 1-5. In this construction the plane of the lips will intersect the collar at both the maximum posterior section 15 and minimum anterior section 19. This device will operate in substantially the same manner as the device previously described, but when the walls of the vagina close, they will close on lips 38 to force the lips together.

Figure 14:
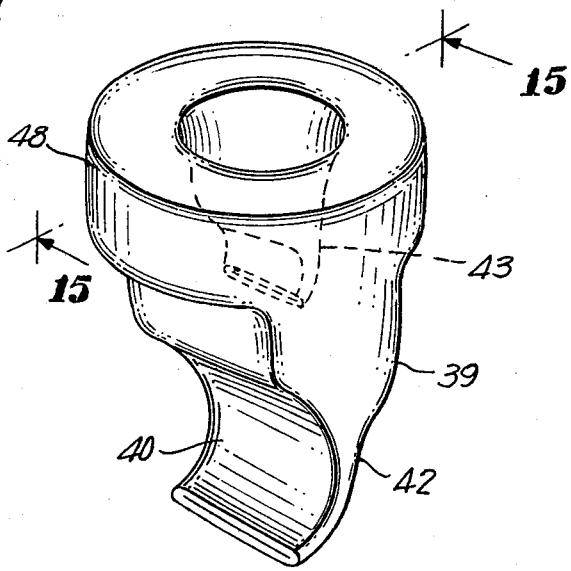
FIG. 14 is a perspective view of a further modified form of cervical cover.
Figure 15:
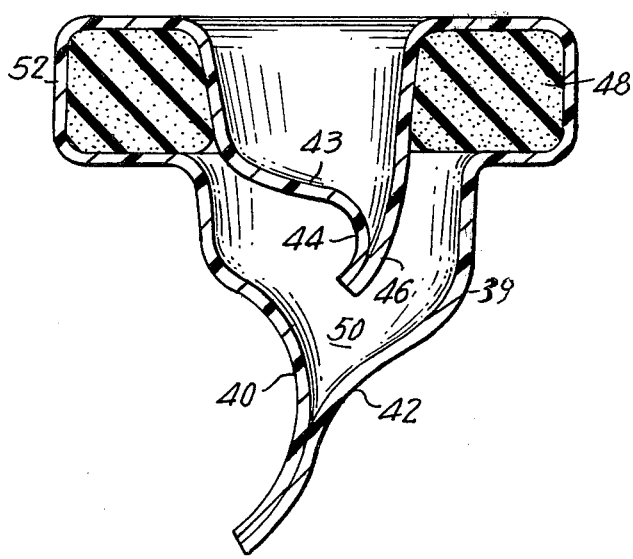
FIG. 15 is a cross-sectional view along the line 15—15 of FIG. 14.

The form of invention illustrated in FIGS. 14 and 15 is similar in principle to the forms previously described, but differs primarily in the provision of a double valve having an outer hollow body 39 with cooperating depending lips 40 and 42 and an inner hollow body 43 having depending lips 44 and 46. Double protection against intrusion of sperm is thus provided without increasing the overall size of the contraceptive.

In contrast to the collars illustrated in FIGS. 1-13, the collar 48 of FIGS. 14 and 15 is preferably made of foam or other soft rubber which in accordance with the principle of the invention is outwardly expandable to engage the walls of the vagina and with a center opening which does not press against the cervix. To prevent rotation of the contraceptive, the shape of the collar is preferably somewhat oval; it likewise can have a square shape with blunted edges. It has been previously pointed out that the vaginal cavity is rarely truly circular with the cervix at the center. It is, therefore, within the scope of this invention to form the inner hollow body 43 offset or eccentric to conform with the anatomy of the user.

A further advantage of the double valve construction is that pressure on the outer valve as by natural movement of the wearer or during intercourse will cause the combined valve to act as a pump to discharge any material from the lower chamber 50. This pump action results from the fact that upon pressure against walls, with lips 44,46 remaining closed, lips 40,42 must open. Self-cleansing of the lower chamber 50 thus results. It is to be understood that the double valve construction can be used with the forms of invention illustrated in FIGS. 1-13, while these forms of my invention may make use of the expandable collar illustrated in FIGS. 14 and 15.

As is most clearly shown in FIG. 15, the entire contraceptive can be simply made from the collar piece 48, about which is adherently disposed a sheet 52 of latex, medical-grade silicone or similar material, surrounding the collar and ending as external valve lips 40,42 and internal valve lips 44,46. However, this specific manner of integrating the lips with the collar is only exemplary; it is within the scope of this invention that the collar section be separately covered with the material forming the valve lips attached to and depending therefrom.

While a double valve as illustrated has been found entirely suitable for contraceptive purposes, the construction illustrated lends itself to the provision of an additional valve of similar configuration within the chamber 50.

Figure 16:
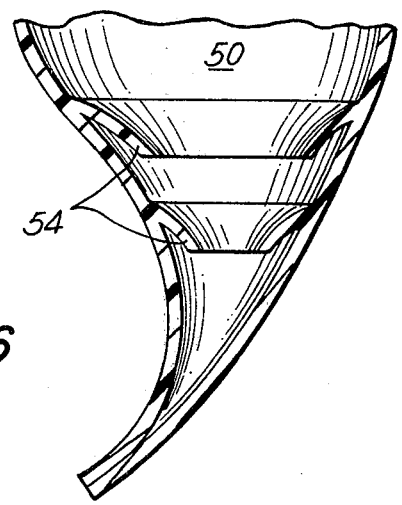
FIG. 16 is a vertical cross-sectional view showing a modified construction of the lips forming part of the cervical cover.

As has been previously pointed out, all forms of the contraceptive device according to the present invention prevent a long path for any sperm which in an unlikely event may penetrate the valve lips. This path may be increased by providing the lower portion of the walls of chamber 50 with a series of small generally annular depending integral extensions 54, as depicted on an exaggerated scale in FIG. 16. It will be at once apparent that this simple modification greatly increases the travel path of any ascending sperm. The modification illustrated in FIG. 16 can, of course, be used with the forms of invention illustrated in FIGS. 1-13 as well as with that illustrated in FIGS. 14 and 15.

The forms of invention described above have proven to be successful for the primary intended purpose, namely to provide a cervical cap which permits vaginal discharge while at the same time serving as an effective contraceptive by preventing travel of semen to the uterus. It has been found, however, when the valve is made of thin flexible material, the possibility of the valve prolapsing does exist, particularly, for example, when contacted by the penis. Obviously if the valve or valves invert, the function of the device to permit vaginal discharge and to prevent movement of the semen has been lost.

Figure 17:
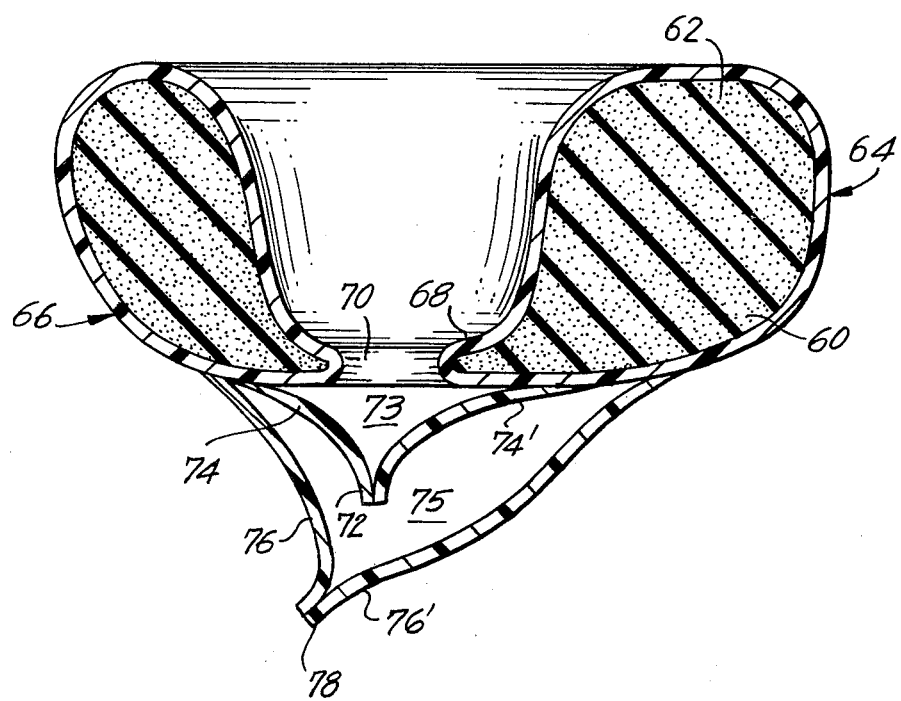
FIG. 17 is a vertical cross-sectional view of yet a further embodiment of my invention.

In the form of invention illustrated in FIG. 17, unwanted prolapsing of the device is prevented. A collar portion 60, preferably of foam rubber, is adherently covered by a sheet 62 of latex, medical grade silicone or similar material. As in the form of invention illustrated in FIGS. 1 and 2, the posterior section 64 of the collar is preferably of greater diameter than the anterior section 66 in conformity with the natural difference in size between the posterior and anterior fornices. However, in contrast with previous forms of the invention, the cover 62 projects inwardly in the form of a flange 68 having a generally circular opening 70 of reduced diameter, but of sufficient size to permit ready discharge from the cervix (not shown) positioned immediately above. The form of invention illustrated in FIG. 17 makes use of the double valve structure as in FIGS. 14-16, but in this case the inner valve 72 of body portion 73 is generally centrally located under opening 70 and is formed by lip sections 74, 74' whose upper ends are adhesively attached to cover material 62. The silicone or other material forming the walls of body portion 73 while flexible are relatively stiff and self-supporting in contrast to the structures previously described. In contrast, the body portion 75 and the lips 76, 76' forming valve 78 are of soft flexible material as in the form of invention shown in FIGS. 14-16. The inner side of these lips may also be formed with internal downward projections in the manner shown in FIG. 16.

It will be seen that while the form of invention illustrated in FIG. 17 has all of the advantages of the devices shown in FIGS. 1-16, internal prolapse of the device is doubly prevented. If valve 78 is pushed upwardly, it will first encounter the substantially stiffer body portion 73. Further upward movement would push both valves against flange 68. The net effect is that prolapse of the valve structure is effectively prevented.

Moreover, ease of placement, comfort of wear and complete safety are characteristics of the present invention. Additionally in the act of intercourse, there are no angles or edges to cause discomfort to the partner.

It will be appreciated that a cervical cover with a valve has been disclosed which will act as an effective contraceptive and can be kept in place for extended periods of time without damage to the cervix.

While specific embodiments of the invention have been described, it will be appreciated that the invention is not limited thereto as many modifications thereto may be made by one skilled in the art which fall within the spirit and scope of the invention.

What I claim is:

1. A female contraceptive device comprising in combination a generally toroidal outwardly expandable collar having an internal wall whose diameter is of sufficient size to surround the cervix and an external wall having an expanded diameter greater than the internal diameter of the vagina in the vicinity of the cervix, whereby said collar when positioned about the cervix is held in place by the pressure of said collar against the vagina and substantially fills the posterior and anterior fornices of the vagina, a hollow body portion integrally attached at its upper end to and depending from said collar below the cervix, and valve means extending downwardly from the lower end of said body portion to permit secretions to pass outwardly therefrom while preventing external entry thereto.

2. A female contraceptive device according to claim 1, in which the vertical cross-sectional area of said toroidal collar is substantially greater on one side than on the diametrically opposite side, whereby said collar may substantially fill both the posterior and anterior fornices when one fornix is larger than the other.

3. A female contraceptive device according to claim 1, in which said body portion depends from the inner wall of said collar.

4. A female contraceptive device according to claim 1, in which said collar is hollow and the inner wall thereof is substantially inflexible compared to said outer wall.

5. A female contraceptive device according to claim 4 wherein the inner wall of the collar is thicker than the outer wall.

6. A female contraceptive device according to claim 1 in combination with spring means outwardly expanding the external wall of said collar.

7. A female contraceptive device according to claim 3 wherein the body portion is dome-shaped and adapted to substantially cover the cervix without applying any substantial pressure thereto when compared to the pressure the collar is adapted to exert on the walls of the vagina to maintain the device in place.

8. A female contraceptive device according to claim 7 wherein the valve means includes two extending lips which are biased together.

9. A female contraceptive device according to claim 8 in which the length of said lips is substantially twice their width.

10. A female contraceptive device according to claim 9 in which the width of said lips approximates the widest diameter of said body portion.

11. A female contraceptive device according to claim 8 wherein the lips are positioned at an angle with respect to the axis of the torus of the collar.

12. A female contraceptive device according to claim 11 wherein the lips are positioned at such an angle so that the lips are proximate said anterior section of the collar.

13. A female contraceptive device according to claim 12 in combination with a string connected to one of said lips and to the anterior section of said collar, whereby said lips can be drawn to said collar on application of force to said string.

14. A female contraceptive device according to claim 8 wherein the lips are interconnected and substantially planar to define a linear opening with an outlet at an end, distal from said body portion.

15. A female contraceptive device according to claim 14 wherein the opening is normally closed.

16. A female contraceptive device according to claim 15 wherein the lips are adapted to separate under the pressure of material discharged from the cervix to permit the material to flow out of the valve.

17. A female contraceptive device according to claim 8 wherein the lips include thicker inclined sections proximate the outlet of the valve.

18. A female contraceptive device according to claim 14 wherein the plane of said lips intersects the collar at the posterior section thereof.

19. A female contraceptive device according to claim 14 wherein the plane of said lips intersects the collar substantially at both the posterior and anterior sections of the collar.

20. A female contraceptive device having a dome-shaped body portion which is adapted to substantially cover the cervix without applying pressure thereon, a collar constructed to fit into and substantially fill the posterior and anterior fornices of the vagina, supporting said body portion and decreasing in cross-sectional area from the posterior section to the anterior section, the posterior and anterior sections being positioned at opposite sides of the collar, means biasing said collar outwardly against the walls of the vagina surrounding the cervix to hold said contraceptive device in position, and valve means including two extending lips biased together, extending from the body portion and proximate to the anterior section and positioned at an angle to the torus of the collar, adapted to permit material to pass outwardly from the body portion without permitting material to enter the body portion through the valve means.

21. A female contraceptive device according to claim 20, in which said collar is hollow and the inner wall thereof is substantially inflexible compared to the outer wall.

22. A female contraceptive device according to claim 21 in which the means for outwardly biasing said collar comprises fluid under pressure within said hollow collar.

23. A female contraceptive device according to claim 22 in which said fluid comprises a liquid foaming agent.

24. A female contraceptive device according to claim 22 in which said fluid comprises a gas.

25. A female contraceptive device according to claim 24 in which said gas is air.

26. A female contraceptive device according to claim 20 wherein the collar completely surrounds the upper perimeter of said body portion.

27. A female contraceptive device according to claim 1, in which said collar is formed of soft compressible rubber.

28. A female contraceptive device according to claim 24, in which said collar has a noncircular shape.

29. A female contraceptive device according to claim 1, in which said hollow body portion is attached to the outer wall of said collar, in combination with a second body portion integrally attached at its upper end to and depending from the inner wall of said collar and within said first body portion, and second valve means extending downwardly from the lower end of said second body portion to permit secretions to pass outwardly therefrom into the first body portion while preventing entry from the body portion into said second body portion.

30. A female contraceptive device according to claim 29 in which said collar is formed of soft compressible rubber, and in which the first and second hollow body portion extends upwardly and about said collar to cover the internal and external walls thereof.

31. A female contraceptive device according to claims 1, 3 or 20, in which the inner wall of said body portion has one or more projections downwardly extending positioned above said valve means.

32. A female contraceptive device according to claim 1, in which said hollow body portion is attached to the outer wall of said collar, in combination with a second body portion integrally attached at its upper end to and depending from the underside of said collar and within said first body portion, and second valve means extending downwardly from the lower end of said second body portion to permit secretions to pass outwardly therefrom into the first body portion while preventing entry from the body portion into said second body portion.

33. A female contraceptive device according to claim 32 in which the first hollow body portion and the first valve means are formed of thin soft, flexible, impervious material, and said second body portion and valve means are formed of flexible impervious material substantially stiffer than the first body portion and valve means.

34. A female contraceptive device according to claim 33 in which said collar is formed with an inwardly extending flange at its lower end having a central opening beneath the cervix.

* * * * *